United States Patent [19]

Jirovs y et al.

[11] Patent Number: 4,488,938
[45] Date of Patent: Dec. 18, 1984

[54] METHOD AND APPARATUS FOR COULOMETRIC MEASUREMENT

[75] Inventors: Ivan Jirovs y; Zorjan Jojko; Ivan Kokoška; Jaroslav Prušek; Václav Trojan, all of Prague, Czechoslovakia

[73] Assignee: Statni vyzkumny ustav ochrany materialu G.V. Akimova, Prague, Czechoslovakia

[21] Appl. No.: 335,095

[22] Filed: Dec. 28, 1981

Related U.S. Application Data

[63] Continuation-in-part of Ser. No. 273,085, Jun. 12, 1981, abandoned.

[30] Foreign Application Priority Data

Jul. 24, 1980 [CS] Czechoslovakia .................... 5236-80
Dec. 29, 1980 [CS] Czechoslovakia .................... 9431-80
Aug. 7, 1981 [CS] Czechoslovakia .................... 5958-81

[51] Int. Cl.³ ...................... G01N 27/26; G01N 27/42
[52] U.S. Cl. .................................... 204/1 T; 204/434; 324/71.1
[58] Field of Search ............... 204/1 T, 195 R, 224 R, 204/129.6, 434; 324/71 R

[56] References Cited

U.S. PATENT DOCUMENTS

| | | | |
|---|---|---|---|
| 2,319,196 | 5/1943 | Anderson et al. | 204/224 R X |
| 2,457,234 | 12/1948 | Herbert et al. | 204/195 R |
| 3,259,840 | 7/1966 | Schaschl et al. | 324/71 R |
| 3,346,477 | 10/1967 | Wolfer | 204/224 R |
| 4,310,389 | 1/1982 | Harbulak | 204/1 T |

FOREIGN PATENT DOCUMENTS 972048 10/1964 United Kingdom ............ 204/224 R

Primary Examiner—G. L. Kaplan
Attorney, Agent, or Firm—Murray Schaffer

[57] ABSTRACT

The thicknesses of metallic coatings on a surface is coulometrically measured employing a probe for storing electrolyte solution provided with a power supply and indicating and controlling circuits. The probe comprises a cylinder defining a chamber for storage of electrolyte and having at one end a nozzle of capillary size surrounded by a gasket or cuff adapted to be placed in abutment against the surface to be tested. The opposite end of the cylinder is connected to a source of oscillating pressure which imposes on the electrolyte a corresponding movement against the working surface.

21 Claims, 2 Drawing Figures

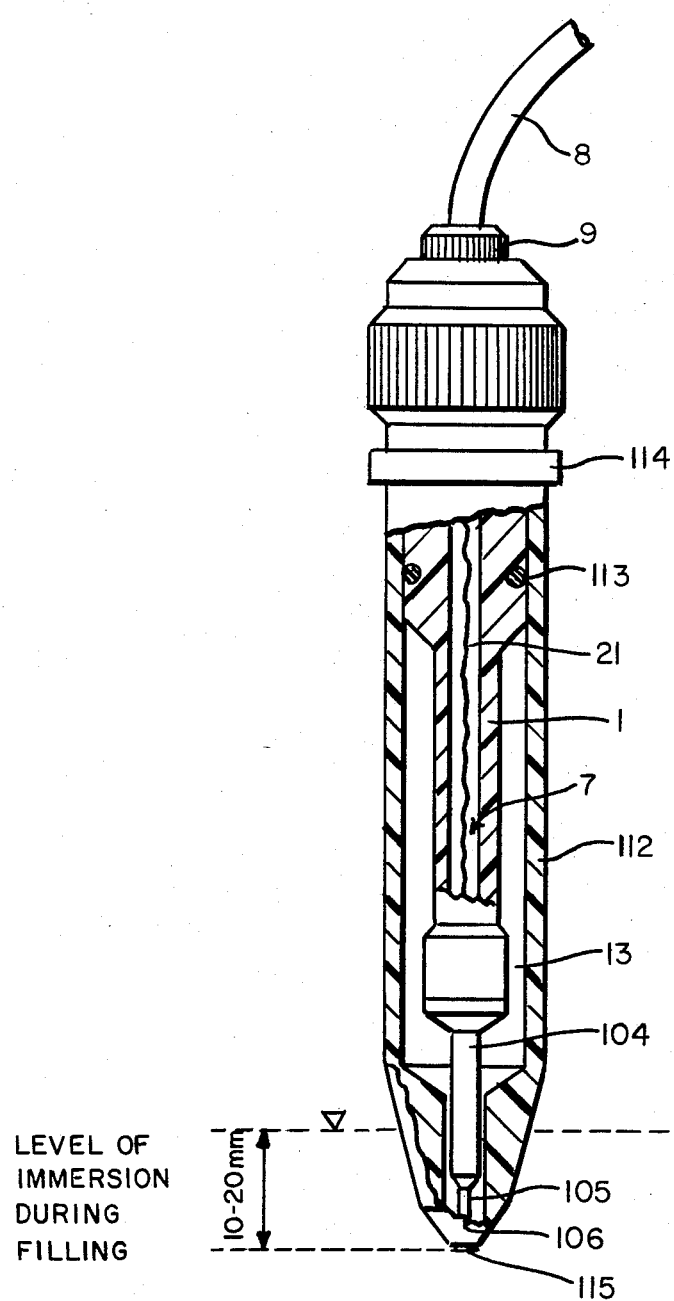

METHOD AND APPARATUS FOR COULOMETRIC MEASUREMENT

RELATED APPLICATION

This is a continuation-in-part of Ser. No. 273,085, filed June 12, 1981, and now abandoned.

BACKGROUND OF THE INVENTION

The present invention relates to a system and apparatus for coulometrically determining the thicknesses of layers of metallic coatings.

At present, there are known and commercially used instruments for measuring coating thicknesses using the coulometric principles based on Faraday's law. The coating thickness is determined by measuring the total quantity of electricity which is necessary for the anodic dissolution of the coating. To do so, the instruments generally employ a cell containing a supply of suitable electrolyte, a power supply necessary for the electrochemical dissolution of the coating, an indicator of the start and completion of the dissolution of the coating, a meter for evaluation of the duration of dissolution whereby the thickness is measured, and means for automatically controlling the entire operation. However, the need to guarantee constant electrochemical condition during the course of the measurement, which is a fundamental requisite for desirable repeatability and accuracy of the apparatus leaves much to be desired. In order to obtain repetitive accuracy and reproducibility of the thickness measurement, a cell must be provided which exactly limits the surface area at which the dissolution of the coating takes place, and furthermore insures the supply of the proper electrolyte to the surface. It is this cell which, in the known systems, has numerous disadvantages.

In several of the known devices, the electrolytic cell comprises an open vessel which is filled manually with the electrolyte, using for example, an "eye" dropper, pipette, syringe or the like. During the measuring period, the electrolyte in the vessel is usually agitated in an attempt to insure proper mixture. Cells of this type require a relatively large working area, for example, a diameter equal to 1.5 to 3.5 mm. Such apparatus do not allow measurements on smaller areas, or a dissolution faster than about 20 to 50 μm per minute.

Another known type of cell is equipped with a separate electrolyte reservoir. The electrolyte is fed from the reservoir to the surface area being measured by a pump in an attempt to ensure the exchange of electrolyte at the site being measured. This type of apparatus allows a reduction in the work area being measured to a diameter of 1 mm, but is somewhat complex and difficult to manage, and often results in losses of electrolyte.

Reference can be made to the following showing the relevant prior art:

Kutzelnigg A.: Die Prufung metallischer Uberzuge, (S.71) E. Leuze Verlag, Saulgau, BRD, 1965

Plog H.: Schichtdickenmessung, (S.19), E. Leuze Verlag, Saulgau, BRD, 1967

Biestek T., Sekowski S.: Methoden zur Prufung metallischer Uberzuge (S.100), E. Leuze Verlag, Saulgau, BRD, 1973

Furthermore, experience with the operation of these types of cells confirms that the electrolyte transfer, at the beginning and at the end of the measuring period, causes difficulties when placing the cell on, or removing the cell from the workpiece being measured, because the electrolyte tends to escape from the cell most easily at these times. In addition, an effective electrolyte exchange is not fully assured during operation since a partial blocking of the area being tested might occur through the formation of an air bubble in the cell. As a result, extensive variations in measurement accuracy and reproducibility may be encountered in practice.

It is the object of the present invention to provide a process and apparatus for producing the electrolyte exchange directly in the vicinity of a defined controlled are so as to significantly increase the measuring accuracy, to provide uniform coating dissolution over the area to be measured, reduce the size of the measured area to a value smaller than those presently used, and to increase the measuring speed.

It is an object of the present invention to provide a cell in the form of a probe which can be manually held and which contains the electrolyte, which insures proper exchange of electrolyte, and reliable definition of the situs.

It is the object of the present invention to provide a probe which will eliminate errors caused by ion depletion and improper mix at the surface of measurement. As a result of this, it is possible to reduce the size of the measurement area, decrease the time required for a measurement, and reuse the same electrolyte for successive measurements.

It is another object to provide a probe which is capable of holding the electrolyte, without loss of liquid, while the probe is removed from the test specimen. As a result, the probe now becomes truly portable, which means that the probe with its electrolyte can be moved, without emptying, from one surface area to another, or from one specimen to another.

It is another object to provide a system wherein the probe can be easily filled, emptied, or rinsed, without the use of auxiliary devices, such as eyedroppers or pipettes.

It is another object to provide a system by which measurements of multi-layer coatings requiring different electrolytes can be done without the use of auxiliary devices.

It is another object to provide a probe system composed to two main components; an outer sleeve, and a removable inner electrolyte storage chamber. This inner chamber can be removed and replaced with another chamber holding a different electrolyte, without disturbing the position of the outer sleeve which is in contact with the test specimen.

It is another object of the present invention to provide a probe which can be used on areas which are substantially inclined from the horizontal.

These objects as well as others together with numerous other advantages, will be apparent from the folowing disclosure.

SUMMARY OF THE INVENTION

According to the present invention, the objects enumerated above are provided by an apparatus for measuring by a coulometric process the thicknesses of metallic coatings on any surface, comprising a probe for storing electrolyte solution, a power supply, indicating and controlling circuits, and a device for placing the electrolyte under oscillating pressure pulsation. The probe comprises a cylinder defining a chamber for storage of electrolyte, which is provided at one end with a jet nozzle having a central tube of capillary size, and with a gasket or cuff member adpated to be placed in abutment against the surface to be tested. The opposite end of the cylinder is connected to the source of oscillating pressure which imposes on the electrolyte a corresponding movement against the working surface.

By containing the electrolyte in a substantially closed cylinder connected to a source of oscillating or pulsed pressure, the electrolyte may be, on the one hand, fully contained in the probe even during periods of non-use simply by arresting the source of oscillation in an under-pressure mode, and, on other hand, fully exchanged at the site of measurement by continuously placing the electrolyte under pulsating pressure. Thereby, stabilization of the working conditions for dissolution and simultaneous manipulation of the device at the area to be measured is greatly simplifed.

In an advantageous embodiment, the cylinder forming the electrolyte storage chamber comprises an inner body element about which a sleeve-like outer element is secured. The outer sleeve is shaped conformingly similar to the cylinder and is provided with a gasket of cuff-like end extending beyond the end of the jet nozzle. The sleeve has a larger diameter than that of the cylinder and is spaced therefrom to provide an annular chamber. The frontal end of the cuff can serve as the gasket abutting the surface of the workpiece, or a gasket can be placed on it. The diameter of the cuff or the gasket secured to its limits the size of the work area and maintains the orifice of the jet nozzle spaced from the surface of the workpiece.

The annular chamber forms a temporary receiving vessel for the electrolyte or fluid issuing from the jet nozzle and allows electrolyte coming from the face of the workpiece to circulate and mix with fresh electrolyte.

Preferably, the outer sleeve and inner cylindrical body element are removably attached so that inner cylinder bodies can be inter-changed without removal of the sleeve element from the workpiece. In this manner, cylinders storing different electrodes may be successively employed to measure successive different layers of coatings.

It is desirable to insure proper mix of partially depleted electrolyte and fresh electrolyte within the storage chamber itself. To this end, a wall is provided within the cylinder forming the storage chamber, which wall is provided with a small hole. Thus, as the electrolyte moves between the two portions of the storage chamber, it is subject to an increase in velocity, thus assuring proper mixing.

Full details of the present invention are set forth in the accompanying description and in the accompanying drawings.

BRIEF DESCRIPTION OF THE DRAWING

In the drawings:

FIG. 2 is a longitudinal sectional view of another probe embodying the present invention.

DESCRIPTION OF THE INVENTION

Figure 1:
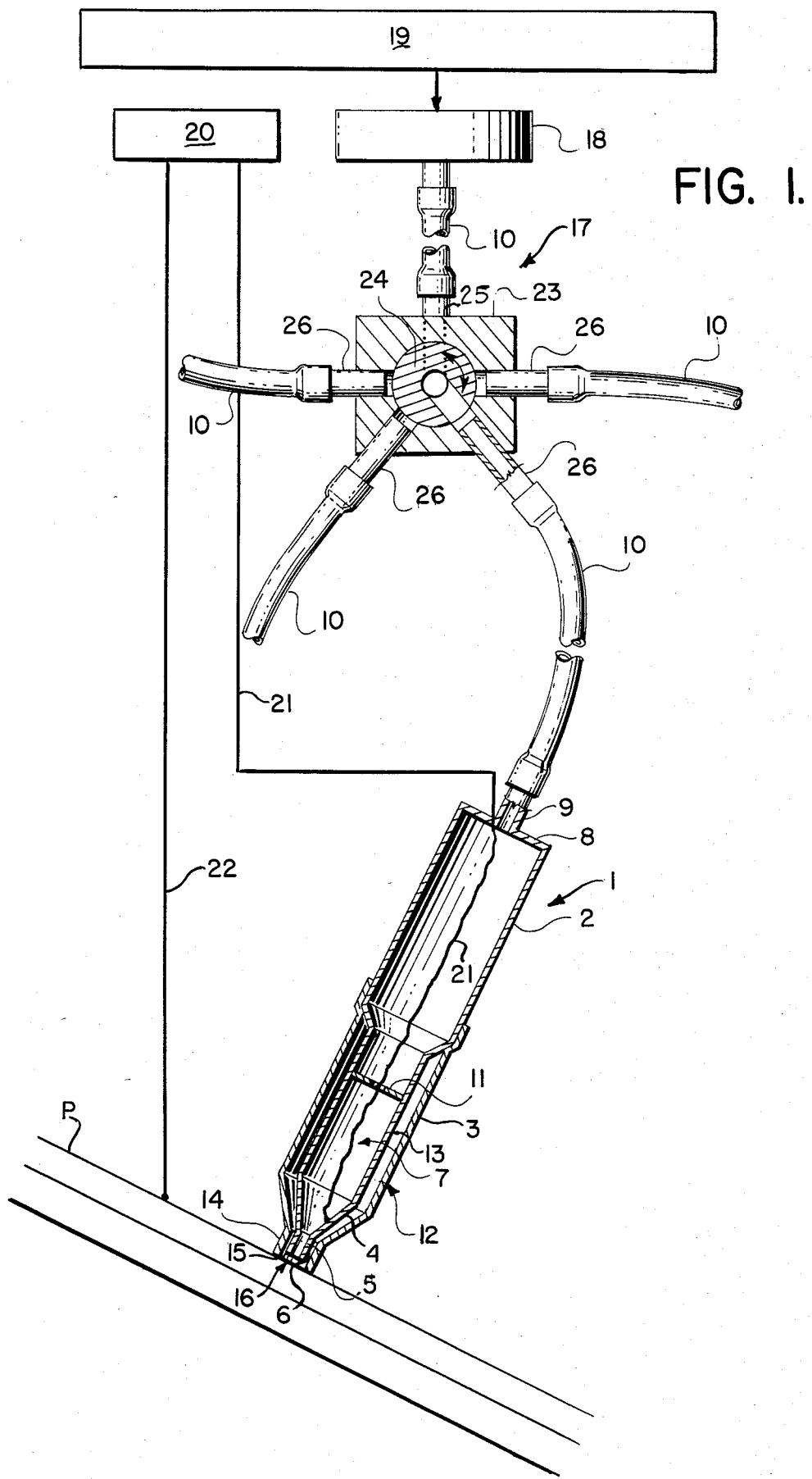
FIG. 1 is a schematic view of an electrolytic system for measuring the thickness of metallic coatings, including a probe therefor embodying the present invention.

As seen in FIG. 1, the apparatus of the present invention comprises a probe, generally defined by the numeral 1, which is adapted to be placed in abutting relationship to the surface of the coated metal workpiece P.

The probe 1 is formed of an inner cylindrical body having a radially enlarged rear portion 2 and a radially smaller end portion 3 the forward end 4 of which is conically tapered and terminates in a jet nozzle 5. The jet nozzle 5 is provided with a capillary bore 6 which communicates with the interior of the smaller portion 3. This smaller portion 3 and the larger portion 2 define a storage chamber 7 for electrolyte or other fluid used. The rear end of the cylinder is closed by an end wall 8 in which is formed a nipple 9 to which is removably attached a flexible conduit 10.

The storage chamber 7 is divided by a wall 11 having a central hole therein which on pulsing of the electrolyte increases the velocity of the electrolyte to effect a positive mixture of all the fluid in the storage chamber.

Secured around the forward portion of the cylinder and its terminal nozzle 5 is a correspondingly shaped sleeve 12 which defines with the exterior wall of the cylinder an annular chamber comprising a temporary receiving chamber 13 for electrolyte. The sleeve 12 is secured at its rear end to the enlarged section of the cylinder so as to be removable therefrom. Suitably O-ring seals, snap closures or threaded closures can be used to removably attach the sleeve 12 to the cylinder. The forward end of the sleeve 12 is formed in the shape of a terminal cuff 14, having a length somewhat longer than that of the interior jet nozzle 5 so that its frontal end 15 protrudes sufficiently so that when it abuts the workpiece, a space 16 is left between the workpiece and the orifice of the capillary bore 6.

The space 16 forms a working chamber in which electro chemical reaction with the surface of the workpiece takes place. The cuff 14 may be provided with a rubber gasket or it may be removable and replaced with a rubber gasket or packing.

Operatively, the cylinder defines a storage chamber having two sections, the rear section serving for the accumulation and main storage of electrolyte, the forward or reduced diameter portion defining another chamber in which electrolyte from the rear section and electrolyte at the tip of the probe are intermixed. The hole in wall 11 intensifies mixing of the eletrolyte as it passes between the two sections of the cylinder and in this way, increases chemical uniformity in the electrolyte and utilization of electrolyte. Preferably the section area of the orifice in wall 11 and that of the orifice in terminal nozzle 5 is in a ratio of between 4:1 and 6:1 for a total volume of electrolyte of 1 to 5 ml.

At this ratio of size between the hole in the wall 11 and the orifice 6 of the jet nozzle, liquid i.e. electrolyte passing through the hole, in either direction is caused to increase in velocity thus assuring a thorough agitation of the contents of the storage chamber, and a thorough mixture of the partially depleted electrolyte from the surface of the workpiece with the fresher electrolyte in the storage chamber. Thus, dilution of depleted electrolyte is enhanced and the total electrolyte has a longer useful life. Thus, a single charge of electrolyte therefore need not be discarded only after a few measurements but may be used for a large number of measurements.

The flexible conduit 10 may be connected to an outlet of a manifold distribution assembly, generally indicated by the numeral 17, the inlet of which is connected to a pneumatic pump 18. The manifold 17 can be dispensed with and the conduit connected directly to the pump, if desired.

The pump 18, produces under response of a control and indicating unit 19 a continuous oscillating stream of pneumatic pulses in alternating overpressure and underpressure modes. The control and indicating unit also regulates a power supply 20 which provides current to a cathode conductor such as a platinum wire 21 extending through the cylinder. The cathode wire 21 is attached to the tapered end 4 of the cylinder, which end is preferably clad in or formed of a suitable metal although the remainder of the cylinder need not. A second or ground conductor 22 is provided.

In operation, the apparatus works as follows:

The probe must first be filled with the electrolyte. This is accomplished by dipping front end of the probe into a container having a supply of the proper electrolyte. The pump 18 is then switched on and if the manifold 17 is employed, the valve is located to connect to the desired probe.

The pump 18 induces a reciprocal pneumatic pressure variation within the probe. The operating frequency is preferably maintained between the value of 1 Hz and 3 Hz. During this procedure, successive expulsion of air from the chamber 7 through the capillary bore 6 and sucking in of electrolyte is accomplished.

The storage chamber becomes filled with the electrolyte much in the manner as a fountain pen is filled. After switching off the pump and arresting it in its underpressure or vacuum mode, a small vacuum caused by the removal of the air maintains the electrolyte in the reservoir chamber 7. Thereafter the filled probe is withdrawn and it can then be placed on the area which is to be tested without any loss of electrolyte.

After placement of the probe 1 onto the area to be tested so that the gasket or cuff 14 squarely abuts the surface of the test specimen the pump 18 is switched on again. The induced reciprocal oscillation is transmitted to the storage chamber 7 displacing the electrolyte through the jet nozzle 5 on to the surface of the workpiece P, the area of which is, of course, limited by the gasket or cuff 14. The electrolyte is on one hand intensively exchanged due to the pulsing action; and, on the other hand, applied with pressure by the pulsating action onto the surface of the area to be tested.

Preferably, it will be advantageous to provide that the area of the jet nozzle, in relation to the area of the gasket or cuff element, which limits the area of testing, be within the range of about 1:3 to 1:15. In this case, an oscillating frequency of between 1 Hz and 3 Hz will supply a sufficient amount of working electrolyte to the surface being tested, and cause a sufficient exchange of electrolyte at that area. This arrangement will also eliminate the possibility that the orifice of the probe is blocked by an air bubble.

At an appropriate time, the power supply 20 is activated, providing suitable current and a conventional coulometric transfer by means of the cathodic wire 21 and the cathode 4 is initiated. The detection, sensing and measurement of the quantity of electricity passed then takes place through the indicating and control element 19, in conventional manner.

Specifically, the electrolyte pumped through the nozzle 5 impinges on the surface of the workpiece, and as excess electrolyte is fed, tends to move upwardly into the temporary receiving chamber 13 formed between the sleeve 12 and the lower portion 3 of the inner cylinder. Thus, as the electro-chemical reaction takes place in the working chamber 16, the depleted electrolyte is forced away from this site allowing fresher electrolyte to progress toward the actual site of dissolution. In this manner, a sufficient amount of undepleted electrolyte is always present at the site, and gas bubbles avoided.

An additional advantage of providing the annular temporary receiving chamber lies in the fact that the probe can be employed to measure surfaces which are inclined substantially to the horizontal. Electrolyte circulating from the face of the workpiece accumulates in the receiving chamber to a depth sufficient to maintain contact with both the metallic cathode and the workpiece surface so that no break in the electrolytic circuit occurs, within a wide range of angles.

After the measurement has been completed both the power supply 20 and the pump 18 are automatically switched off. The pump is regulated so that it comes to rest in its underpressure mode. This causes the automatic transfer of the working electrolyte back into the storage chamber 7. The probe can then be removed from the workpiece without any loss of the working electrolyte. The detector probe can then be transferred to another measurement area on the same piece, or a different test specimen without the need for replacement or exchange of the working electrolyte.

Complete retraction of the electrolyte into the storage chamber is assured by a combination of the underpressure on top of the electrolyte, caused by the arresting of the pump in its underpressure mode and the overpressure created in the temporary receiving chamber 13 caused by the compression of the air trapped therein by the circulating fluid. The spring action of the trapped air forces the electrolyte back into the storage chamber where it is held due to the underpressure therein. Consequently, none of the electrolyte is lost when the probe is removed from the workpiece or subsequently placed on a new workpiece. Further, this enables the inner cylinder to be removed from the outer cylinder, also without loss of electrolyte, and its replacement with a different inner cylinder containing a different electrolyte.

In this manner, a sequential measurement of successive layers of different metals can be accomplished without removing the outer sleeve from the site of the workpiece.

In referring to over and underpressure, great pressures in excess of atmospheric pressure or great vacuums are not necessarily required, due to the overall small size of the probe and the small volume of electrolyte employed. Only a small difference in pressure between that at the top of the electrolyte in the storage chamber, and the pressure on the electrolyte at the orifice of the jet nozzle is necessary to effect either pulsation or retraction.

It is preferable that the length of the capillary 6 be between 3 and 12 mm and that the ratio between the area of the capillary 6 and that of area of the orifice of the gasket or cuff 14 be between 1:3 to 1:15. As a result of this ratio, accurate capillary action is obtained with a pulse rate of between 1 Hz and 3 Hz. A further advantage of the present invention lies in the fact that the cathode conductor is placed inside the probe in direct contact with the electrolyte pumping through the probe as a result of the oscillating pressure applied on the electrolyte.

Returning to the drawing, the manifold distribution assembly 17 comprises a distribution valve 23 provided with a rotatable slide member 24, a fixed inlet 25 connectable to the pneumatic pump 18 and a plurality of fixed outlets 26, each of which is adaptable for connection to a flexible conduit 10 associated with an individual cylindrical body. Manipulation of the rotary slide 24 will enable selection of the particular cylindrical body for operation. As a consequence, individual cylindrical bodies may be initially filled with a particular electrolyte, as for example, electrolyte for dissolution of Cu, Cr, Ni respectively. An operator can, thus, easily determine the thickness of successive layers of a multi-layer coating by removing the inner body from the sleeve of the probe being used and replacing it with another inner body having the proper electrolyte, without necessarily removing the outer sleeve from the site on the workpiece. One cylindrical body can be filled with distilled water, and used to rinse the site of the workpiece and/or sleeve before initiating a second electrolytic measurement.

Thus, the invention makes possible repetitive measurements of the thickness of both single-layer or multi-layer coating with maximum utilization of the electrolyte and with greater accuracy. The probe is designed as basic equipment for coulometric measuring system, not only of the type designed in the aforementioned pending application, but with other systems as well.

FIG. 2 shows another embodiment of the probe which is similar to that of FIG. 1. Similar numerals depict similar parts. This embodiment differs in the dimension of the inner cylinder body 1, which in FIG. 2 is substantially smaller in radius and does not include a dividing wall. The nozzle portion is somewhat longer axially and comprises a metallic section 104 which forms the cathode and a plastic tip 105 which forms a jet nozzle. Both the metal cathode and plastic tip have a capillary bore 106 which need not be of the same diameter. The outer sleeve 112 extends substantially the full length of the probe and is provided with an O-ring seal 113 and a ring connector 114. The tip of the probe is provided with a rubber gasket 115 which is removable. Operation is similar as in the previously described embodiment.

The present invention provides conditions for a uniform anodic dissolution of the coating on the surface of the test specimen during the entire time interval during which dissolution takes place and for obtaining reproduceable and accurate measurements. Increased speeds of dissolution at a rate greater than heretofore known has also been obtained.

Optimum setting of the operating pulse frequency for pumping the electrolyte solution, their time behavior and amplitude, and of the ratio of nozzle diameter in the working chamber to the diameter of the area being tested can likewise be obtained by the present invention by simple selection of the oscillator control and the probe dimensions.

In addition, the entire area and volume for the entire interval of measurement is optimized. At static connection of the dissolving current supply, errors in determination, generally caused by variable conditions frequent in conventional apparatus, is avoided.

Although the invention is illustrated and described with reference to preferred embodiments thereof, it is to be expressly understood that it is in no way limited to the disclosure of such embodiments, but it is capable of numerous modifications within the scope of the appended claims.

What is claimed:

1. In a system for coulometrically measuring the thickness of a metallic coating on the surface of a workpiece, a probe comprising a substantially closed cylindrical inner body defining a chamber for the storage of electrolyte and an outer sleeve shaped conformingly to said inner body, said outer sleeve being sealingly secured at its rear end to said inner cylindrical body and forming an annular chamber therewith sealed at the rear end therewith, said cylindrical inner body being provided at a forward end with a jet nozzle, said outer sleeve having a cuff surrounding said nozzle for placement in contact with the surface of said workpiece to seal the area about said jet nozzle, means connected to the rear end of said cylinder for imposing oscillating pressure pulses on said electrolyte whereby said electrolyte is caused to impinge on the surface of said workpiece and circulate into said annular chamber.

2. The probe according to claim 1 wherein said nozzle has a passage of capillary size.

3. The probe according to claim 1 wherein said cuff is elastic.

4. The probe according to claim 3 wherein said cuff is removable.

5. The probe according to claim 1 wherein the ratio of the section area of the orifice of said nozzle and the section area of the orifice of said cuff is in the range of between 1:3 to 1:15.

6. The probe according to claim 1 wherein means for imposing the oscillating pressure on said electrolyte comprises a pneumatic pump.

7. The probe according to claim 6 wherein said pump and cylinder are connected by an elongated flexible conduit.

8. The probe according to claim 6 including a manifold distribution assembly having an inlet connected to said pump and a plurality of outlets adapted for connection respectively to the cylinder of a probe.

9. The probe according to claim 1 including a conductor extending through said cylinder and connected to said nozzle.

10. The probe according to claim 1 including a wall located within said cylinder and dividing said cylinder into two sections, said wall having a hole therein for the passage of electrolyte between said sections.

11. The probe according to claim 10 wherein the ratio of sectional area of said hole and the sectional area of said nozzle is in a range between 4:1 to 6:1.

12. The probe according to claim 1 wherein the outer sleeve is removably attached to the inner cylindrical body.

13. The probe according to claim 1 wherein a portion of said nozzle is metallic and forms a cathode and a portion of said nozzle is plastic.

14. A method for coulometrically measuring the thickness of a metallic coating on the surface of a workpiece comprising the steps of storing electrolyte within a substantially closed cylinder having a capillary opening at one end a sleeve surrounding said cylinder and defining therewith an annular chamber sealed at its upper end and a cuff surrounding said capillary opening, applying an oscillating pressure pulse on the electrolyte within said cylinder to correspondingly eject and retract said electrolyte through said capillary opening against the surface of said workpiece and into said annular chamber while simultaneously applying an electrical current through said electrolyte to effect an electrolytic reaction with the metal on the surface of said workpiece.

15. The method according to claim 14 wherein said oscillation is maintained between 1 Hz and 3 Hz.

16. The method according to claim 14 wherein said oscillating pressure pulses are applied by establishing an overpressure and underpressure on said electrolyte stored within the cylinder relative to the pressure acting on said electrolyte at said capillary opening.

17. The method according to claim 16 wherein said source of oscillating pulse on said electrolyte is arrested in a relative underpressure mode thereby causing said electrolyte to be retracted into said cylinder.

18. In a system for coulometrically measuring the thickness of a metallic coating on the surface of a workpiece, a probe comprising a substantially closed cylinder defining a chamber for the storage of electrolyte, a wall located within said cylinder and dividing said cylinder into two sections, said wall having a hole therein for the passage of electrolyte between said sections, said cylinder being provided at one end with a nozzle, a cuff surrounding said nozzle adapted to be placed in contact with the surface of said workpiece, said cylinder having at its other end means for imposing oscillating pressure pulses on said electrolyte.

19. The probe according to claim 18 wherein the ratio of sectional area of said hole and the sectional area of said nozzle is in a range between 4:1 to 6:1.

20. In a system for coulometrically measuring the thickness of a metallic coating on the surface of a workpiece, a probe comprising a substantially closed cylinder defining a chamber for the storage of electrolyte, said cylinder being provided at one end with a nozzle, a cuff surrounding said nozzle adapted to be placed in contact with the surface of said workpiece, said cylinder having at its other end means for imposing oscillating pressure pulses on said electrolyte, said nozzle having a portion which is metallic and forms a cathode and a portion which is plastic.

21. In a system for coulometrically measuring the thickness of a metallic coating on the surface of a workpiece, a probe comprising a substantially closed cylinder defining a chamber for the storage of electrolyte, said cylinder being provided at one end with a nozzle, a cuff surrounding said nozzle adapted to be placed in contact with the surface of said workpiece, said cylinder having at its other end means for imposing oscillating pressure pulses on said electrolyte, said means comprising a pneumatic pump and a manifold distribution assembly having an inlet connected to said pump and a plurality of outlets adapted for connection respectively to the cylinder of a probe.

* * * * *

UNITED STATES PATENT AND TRADEMARK OFFICE
CERTIFICATE OF CORRECTION

PATENT NO. : 4,488,938
DATED : December 18, 1984
INVENTOR(S) : Ivan JIROVSKY et al It is certified that error appears in the above-identified patent and that said Letters Patent are hereby corrected as shown below:

On the cover sheet [75] the name of the inventors should read:

--Ivan Jirovsky; Zorjan Jojko; Ivan Kokoska; Jaroslav Prusek;

Vaclav Trojan, all of Prague, Czechoslovakia --

Signed and Sealed this

Sixteenth Day of July 1985

[SEAL]

Attest:

DONALD J. QUIGG

Attesting Officer     Acting Commissioner of Patents and Trademarks